(12) United States Patent
Akahoshi

(10) Patent No.: US 7,601,135 B2
(45) Date of Patent: Oct. 13, 2009

(54) MULTI-PORT INFUSION SLEEVE

(76) Inventor: Takayuki Akahoshi, 1-11-7-2603, Tsukuda, Chuoku, Tokyo (JP) 104-0051

( * ) Notice: Subject to any disclaimer, the term of this patent is extended or adjusted under 35 U.S.C. 154(b) by 559 days.

(21) Appl. No.: 11/069,772

(22) Filed: Mar. 1, 2005

(65) Prior Publication Data

US 2006/0200067 A1    Sep. 7, 2006

(51) Int. Cl.
*A61F 9/007* (2006.01)
(52) U.S. Cl. ........................................ 604/22
(58) Field of Classification Search ........... 604/274, 604/22, 27, 264; 606/107
See application file for complete search history.

(56) References Cited

U.S. PATENT DOCUMENTS

| | | | | |
|---|---|---|---|---|
| 4,643,717 A | * | 2/1987 | Cook et al. | 604/22 |
| 5,084,009 A | * | 1/1992 | Mackool | 604/22 |
| 5,151,084 A | * | 9/1992 | Khek | 604/22 |
| 5,256,147 A | * | 10/1993 | Vidal et al. | 604/158 |
| 5,286,256 A | * | 2/1994 | Mackool | 604/22 |
| 5,354,265 A | * | 10/1994 | Mackool | 604/22 |
| 5,505,693 A | * | 4/1996 | Mackool | 604/22 |
| 5,520,193 A | * | 5/1996 | Suzuki et al. | 600/577 |
| 5,533,957 A | * | 7/1996 | Aldea | 600/16 |
| 5,597,377 A | * | 1/1997 | Aldea | 600/16 |
| 5,634,912 A | * | 6/1997 | Injev | 604/264 |
| 5,645,530 A | * | 7/1997 | Boukhny et al. | 604/22 |
| 5,873,851 A | * | 2/1999 | Nilsson | 604/43 |
| 5,879,356 A | * | 3/1999 | Geuder | 606/107 |
| 6,117,151 A | * | 9/2000 | Urich et al. | 606/169 |
| 6,159,175 A | * | 12/2000 | Strukel et al. | 604/22 |
| 6,299,591 B1 | * | 10/2001 | Banko | 604/22 |
| 6,605,054 B2 | * | 8/2003 | Rockley | 604/22 |
| 6,830,555 B2 | * | 12/2004 | Rockley et al. | 604/22 |
| 7,014,629 B2 | * | 3/2006 | Mackool | 604/274 |
| 7,094,229 B2 | * | 8/2006 | Boukhny et al. | 604/500 |
| 2003/0004455 A1 | * | 1/2003 | Kadziauskas et al. | 604/27 |
| 2004/0153026 A1 | * | 8/2004 | Mackool | 604/22 |
| 2008/0300531 A1 | * | 12/2008 | Gills, Jr. | 604/22 |

* cited by examiner

*Primary Examiner*—Nicholas D Lucchesi
*Assistant Examiner*—Aarti Bhatia
(74) *Attorney, Agent, or Firm*—Jerry A. Schulman

(57) ABSTRACT

An infusion sleeve for use with a phacoemulsification handpiece has a hollow body with an open end by which the sleeve is attachable to the handpiece and an open tip through which a phacoemulsification needle is passed. Irrigating liquid is directed from the handpiece through the sleeve. At least three discharge ports are formed in the sleeve to provide increased flow of irrigating liquid proximate the sleeve tip. The ports may differ in size, shape and positioning on the sleeve.

12 Claims, 6 Drawing Sheets

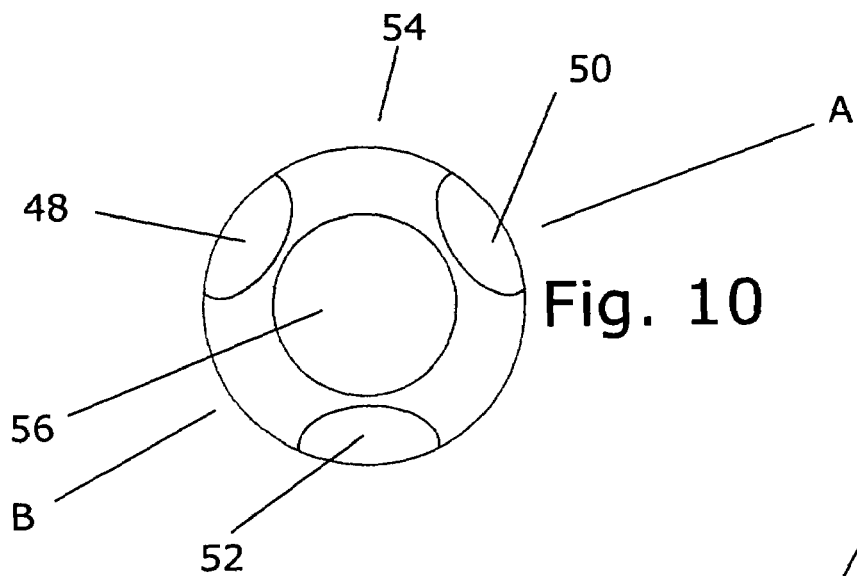
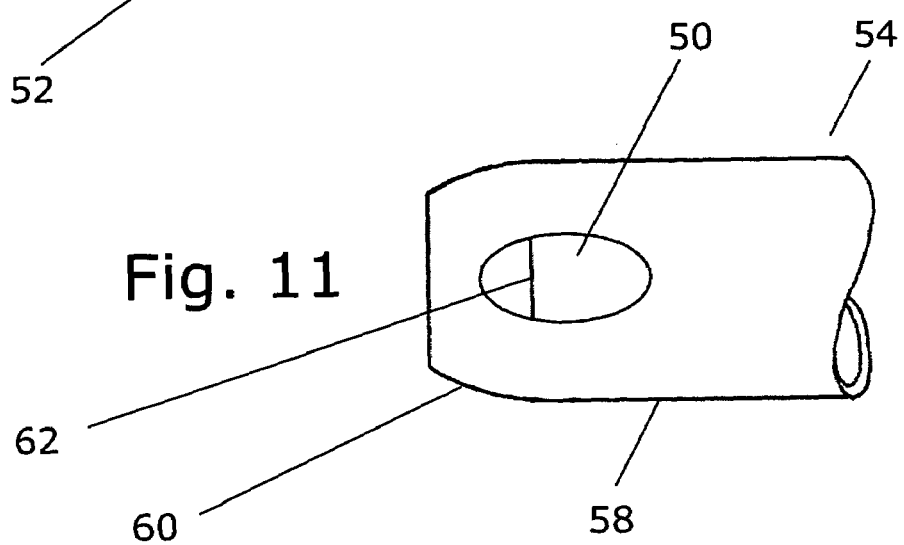
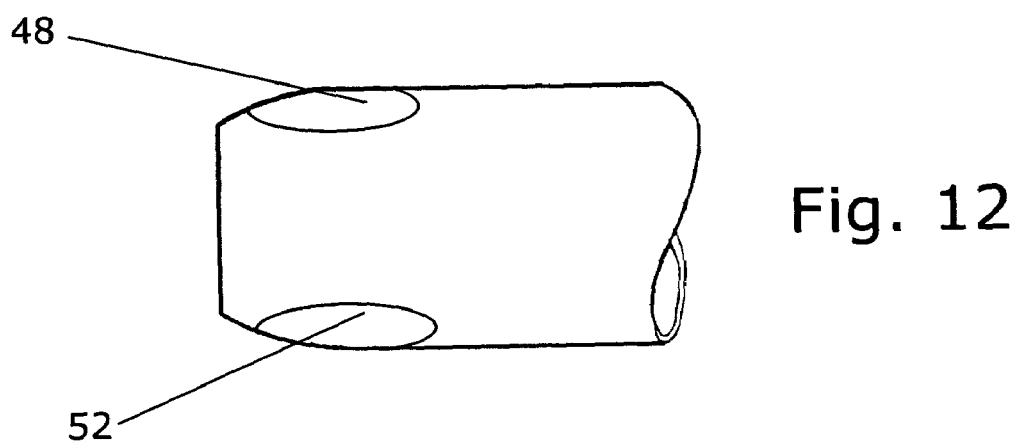

MULTI-PORT INFUSION SLEEVE

BACKGROUND OF THE INVENTION

This invention relates to surgical instruments and surgical techniques used in eye surgery and more particularly, to the technique of phacoemulsification apparatus and methods for their use.

A common ophthalmological surgical technique is the removal of a diseased or injured lens from the eye. Earlier techniques used for the removal of the lens typically required a substantial incision to be made in the capsular bag in which the lens is encased. Such incisions were often on the order of 12 mm in length.

Later techniques focused on removing diseased lenses and inserting replacement artificial lenses through as small an incision as possible. For example, it is now a common technique to take an artificial intraocular lens (IOL), fold it and insert the folded lens through the incision, allowing the lens to unfold when it is properly positioned within the capsular bag. Similarly, efforts have been made to accomplish the removal of the diseased lens through an equally small incision.

One such technique is known as phacoemulsification. A typical phacoemulsification tool includes a hollow needle to which electrical energy is applied to vibrate the needle at ultrasonic frequencies in order to fragment the diseased lens into small enough particles to be aspirated from the eye. Commonly, an infusion sleeve is mounted around the needle to supply irrigating liquids to the eye in order to aid in flushing and aspirating the lens particles.

It is extremely important to properly infuse liquid during such surgery. Maintaining a sufficient amount of liquid prevents collapse of certain tissues within the eye and attendant injury or damage to delicate eye structures. As an example, endothelial cells can easily be damaged during such collapse and this damage is permanent because these cells do not regenerate. One of the benefits of using as small in incision as possible during such surgery is the minimization of leakage of liquid during and after surgery and the prevention of such a collapse One way to ensure infusion of a sufficient amount of liquid within the eye during an operation is to increase liquid flow through the infusion sleeve. This can cause an increase in the Reynolds number of the infusion liquid to the point where the liquid flow become turbulent which can, in itself cause damage to the eye.

Instruments using various types of infusing sleeves are well known and well-represented in the art and exemplify the attempts made by others to address the problem of maintaining an adequate flow of irrigating liquid without causing damage to the eye.

U.S. Pat. No. 4,643,717 (Cook et al) teaches and describes an aspiration fitting adapter formed as a sleeve concentric to the phaco needle and having a pair of bilaterally opposed discharge ports formed proximate the end of the sleeve to infuse irrigating liquid into the eye.

U.S. Pat. No. 5,151,084 (Khek) teaches and describes an ultrasonic needle with an infusion sleeve that includes a baffle. The sleeve of Khek also fits concentrically about the needle and allows the needle to protrude a substantial distance therefrom while providing pair of discharge ports bilaterally opposed to each other near the terminus of the sleeve.

U.S. Pat. No. 6,117,151 (Urich et al) teaches and describes an eye incision temperature protection sleeve fitted concentrically about a needle and having a single discharge port through which irrigating liquid is passed.

U.S. Pat. No. 6,605,054 (Rockley) teaches and describes a multiple bypass port phaco tip having multiple aspiration ports and a single discharge port to infuse liquid into the eye.

U.S. Pat. No. 5,879,356 (Geuder) teaches and describes a surgical instrument for crushing crystalline eye lenses by means of ultrasound and for removing lens debris by suction which demonstrates the use of a sleeve positioned concentric to the needle and having a pair of discharge ports formed thereon.

A series of patents issued to Richard J. Mackool illustrates further variations of irrigating sleeves. Mackool forms the sleeve with a somewhat flattened cross-section configuration intended to more closely approximate the shape of the incision through which the sleeve is inserted into the eye. This cross-section can be seen at FIG. 3 of U.S. Pat. No. 5,084,009.

U.S. Pat. No. 5,084,009 (Mackool) teaches and describes a liquid infusion sleeve for use during eye surgery with the sleeve having a flattened cross-section and having a pair of infusion ports formed on the forward portion of the flattened section.

U.S. Pat. No. 5,286,256 (Mackool) teaches and describes a liquid infusion sleeve having a free-floating rigid sleeve surrounding a needle which is intended to prevent the outer flexible sleeve from collapsing onto the needle.

U.S. Pat. No. 5,354,265 (Mackool) teaches and describes a liquid infusion sleeve showing yet another construction intended to keep the outer flexible infusion sleeve from collapsing onto the vibrating needle.

U.S. Pat. No. 5,505,693 (Mackool) teaches and describes a method and apparatus for reducing friction and heat generation by an ultrasonic device during surgery incorporating a needle support to prevent collapse of the outer flexible sleeve.

The Mackool patents are characterized by a pair of discharge ports formed at the distal end of the sleeve through which irrigating liquid is passed into the eye during the operation.

U.S. Pat. No. 5,645,530 (Boukhny) teaches and describes a phaco emulsification sleeve, one variation of which has a bellows portion attached to a discharge port ring which directs an annular flow of liquid around the needle and into the eye. The use of the bellows is intended to allow the sleeve to absorb spikes in liquid pressure during the operation.

U.S. Pat. No. 5,634,912 (Injev) teaches and describes an infusion sleeve having a rotating tip to allow the phaco needle to be repositioned during surgery. The top also has a single discharge port for infusing liquid during surgery.

Published U.S. Patent Application No. 2003/0004455 (Kadziauskas) teaches and describes a bi-manual phaco needle using separate emulsification and aspiration needles inserted into the eye simultaneously during surgery.

While the foregoing references describe the problems faced during phaco emulsification with respect to supplying the eye with an adequate amount of irrigating liquid, they do not particularly point out nor describe apparatus nor methods for safely increasing the flow of liquid without attendant side effects. Accordingly, the need exists for an improved infusion sleeve which allows for a greater volume of liquid to be infused into the eye while avoiding the problems described in the prior art with respect to increased pressure, turbulence and the like.

The need also exists for such improved infusion sleeves to be simple in construction, efficient in operation and economical to manufacture.

In accordance with a preferred embodiment of the present invention, a phaco infusion sleeve has at least three infusion liquid discharge ports formed proximate the tip of the sleeve. In a second preferred embodiment, four such ports are formed. Preferably, the ports are formed equidistantly about the circumference of the sleeve and, preferably are oval in shape with the major axis of the oval parallel to the major axis of the sleeve. In a second embodiment, four such ports are formed equidistantly about the circumference of the sleeve and, preferably, the ports are oval with the major axis of each oval substantially parallel to the major axis of the sleeve.

While the following describes a preferred embodiment or embodiments of the present invention, it is to be understood that this description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

These and further aspects of the present invention will become apparent upon consideration of the accompanying drawing figures in which:

BRIEF DESCRIPTION OF THE DRAWINGS

FIG. 10 is an end view of a second embodiment of the present invention showing three equidistantly spaced discharge ports;
FIG. 11 is a lateral view of a portion of the sleeve shown in FIG. 10;
FIG. 12 is a bottom view of a portion of the sleeve shown in FIG. 10.

DETAILED DESCRIPTION OF THE DRAWINGS

Figure 1:
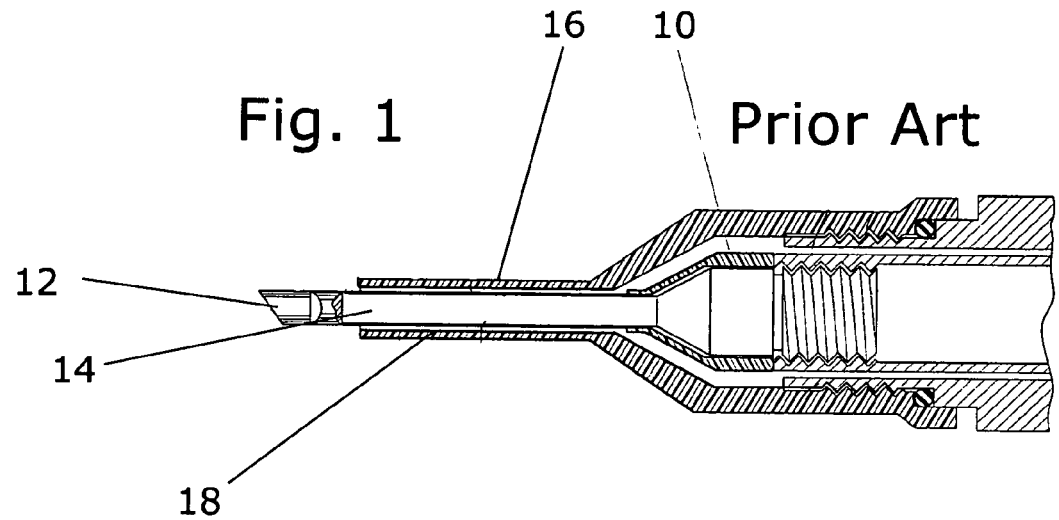
FIG. 1 is a first prior art illustration of an irrigation sleeve.

Referring now to FIG. 1 the numeral 10 indicates generally a partial sectional view of a prior art phacoemulsification hand piece having a needle 12 defining a hollow internal chamber 14 through which irrigation liquid and emulsified particles of a lens are aspirated from the capsular bag. As seen in FIG. 1, an irrigating sleeve 16 is mounted to hand piece 10, from which needle 12 protrudes. Sleeve 16 communicates with an irrigation liquid supply within handpiece 10 and provides irrigating liquid to the capsular bag through an annular channel 18 formed between needle 12 and sleeve 16.

Figure 2:
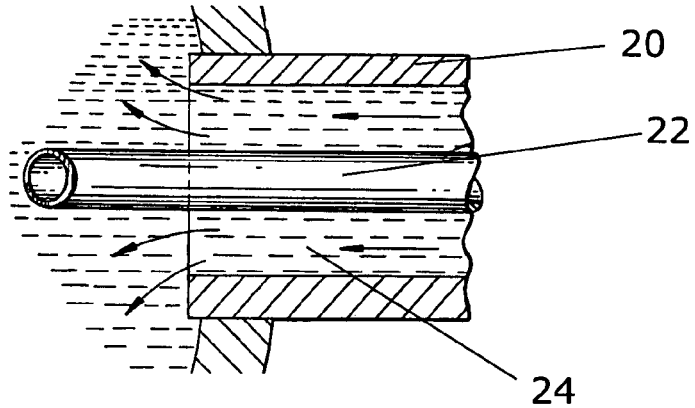
FIG. 2 is a second illustration of a prior art irrigation sleeve.

Referring now to FIG. 2, an enlarged partial sectional view of a second prior art phacoemulsification apparatus is shown having a sleeve 20 surrounding a hollow needle 22 and defining therebetween an annular channel 24 as a conduit for irrigating liquid.

Both FIG. 1 and FIG. 2 show a prior art apparatus with the flow of irrigating liquid directed annularly about the periphery of the hollow phaco needle.

Figure 3:
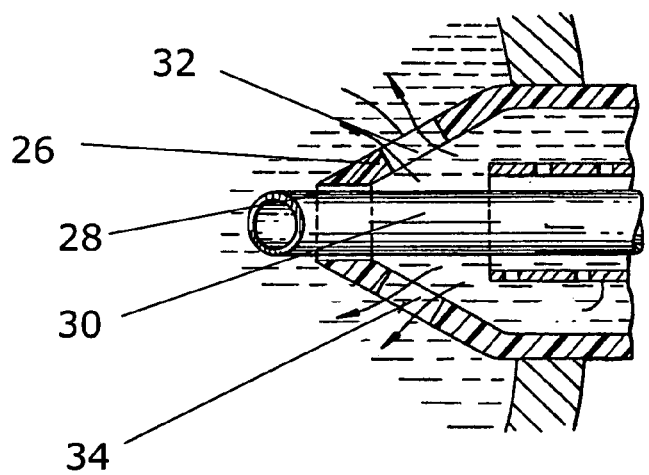
FIG. 3 is a third illustration of a prior art irrigation sleeve.

Referring now to FIG. 3, a partial sectional view of a second embodiment of the apparatus of FIG. 2 is shown where the infusion sleeve 26 tapers to form an opening 28 through which needle 30 extends. A pair of infusion ports 32, 34 are formed in the angled side walls of sleeve 26 to form a pathway for infusing liquid.

The embodiments shown in FIGS. 2 and 3 are taken from U.S. Pat. No. 5,084,009 and as discussed above, it appears that ports 32, 34 are formed along the flattened portion of sleeve 26 and are the only infusion ports present.

I have found, surprisingly, that the addition of one or more infusion ports results in a higher flow rate of infusing liquid without causing problems of damage to cellular structures within the eye such as the endothelial cells and which preserves the desirable flow characteristics of the infusing liquid. I have also found that a higher flow rate under these flow conditions provides additional unexpected benefits. For example, the flow from an additional port may be directed to stretch and deepen the capsular bag, decreasing the risk of posterior capsule rupture.

FIGS. 4-18 demonstrate the modifications and variations to an existing phaco infusion sleeve. For purposes of clarity, only the tip portion of each such sleeve will be shown, it being understood that the sleeve is fitted coaxial to a phaco needle which extends outward from the sleeve.

Figure 4:
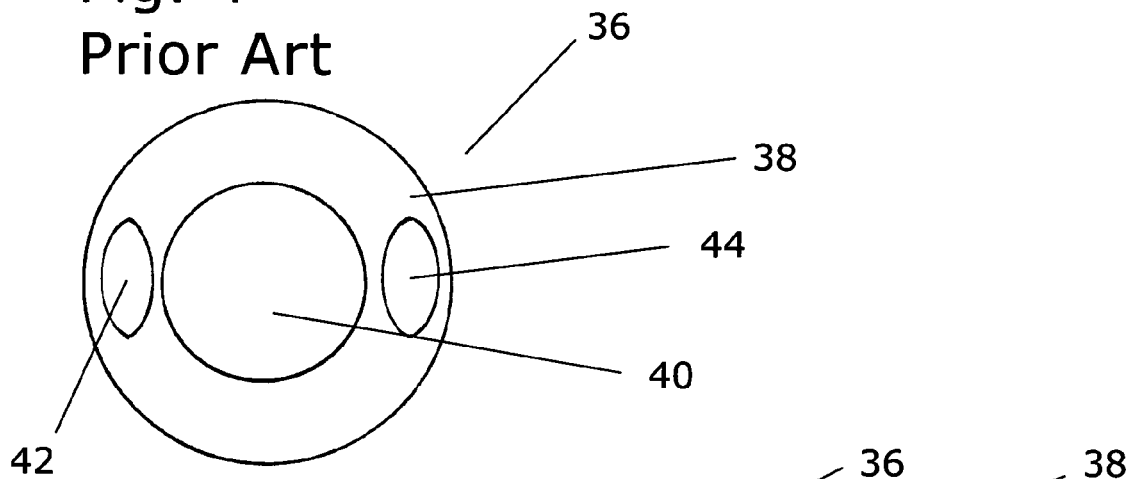
FIG. 4 is an end view of an irrigation sleeve having two circular and bilaterally opposed discharge ports.

FIG. 4 is an end view of a known prior art infusion sleeve 36 having an outer sleeve wall 38, a central passage 40 to accommodate the phaco needle and a pair of diametrically opposed infusion ports 42, 44. This is the present arrangement on a currently available infusion sleeve.

Figure 5:
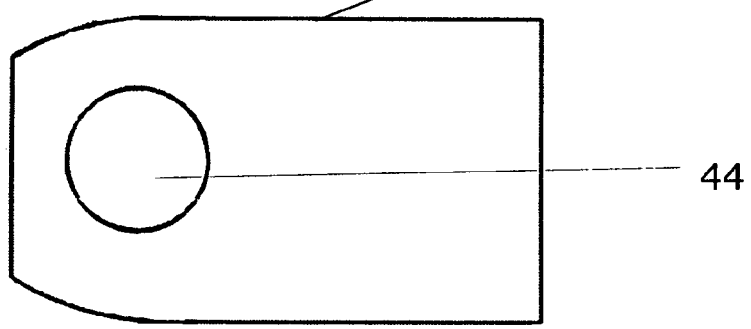
FIG. 5 is a lateral view of a portion of the sleeve shown in FIG. 4.
Figure 6:
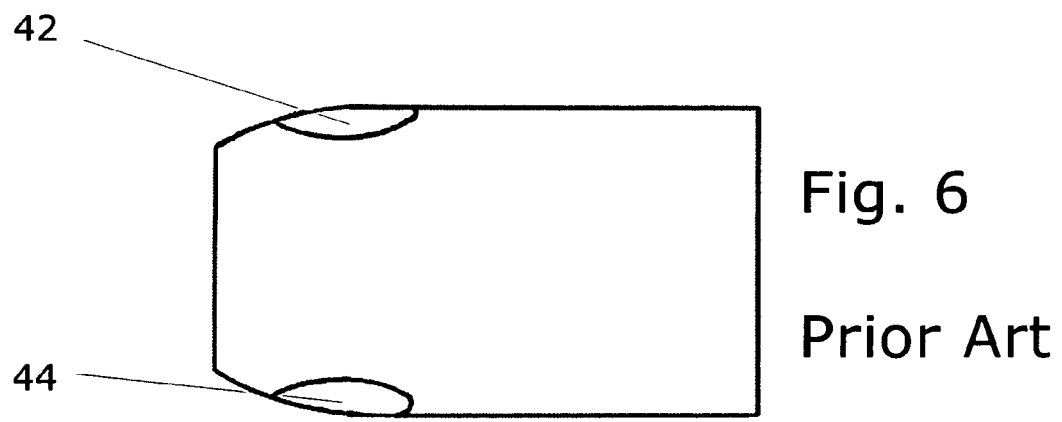
FIG. 6 is a top view of a portion of the sleeve shown in FIG. 4.

FIG. 5 is a lateral side view of the sleeve tip shown in FIG. 4, demonstrating that the infusion port 44 is circular in shape. FIG. 6 is a top view of the tip of FIG. 4 again demonstrating the diametrically opposed positions of infusion ports 42, 44.

Figure 7:
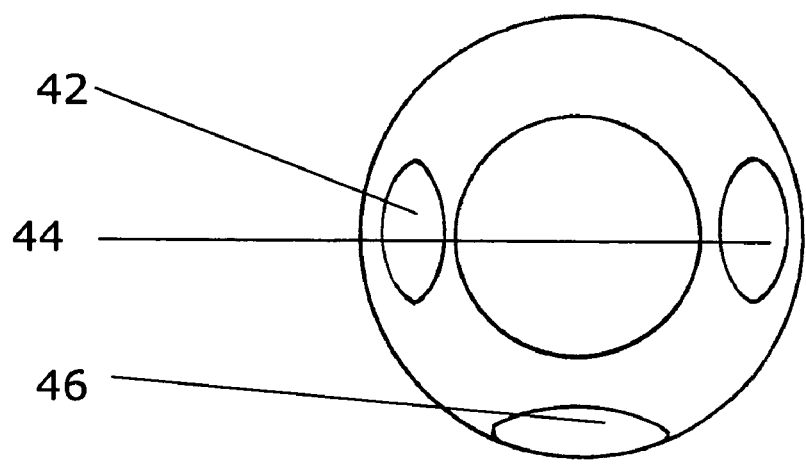
FIG. 7 is an end view of a modified version of the sleeve shown in FIG. 6.
Figure 8:
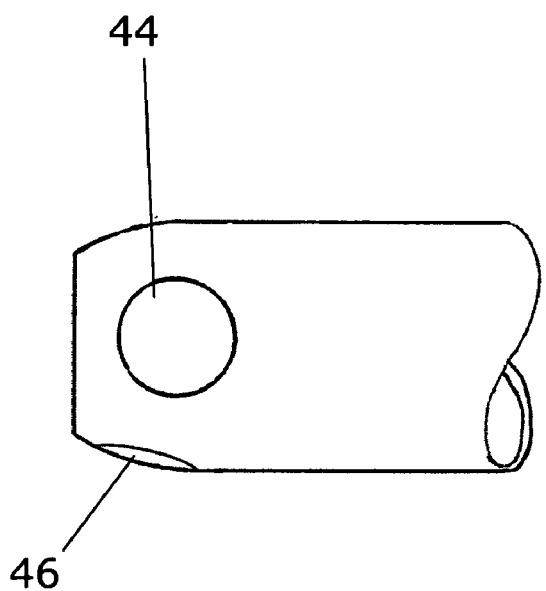
FIG. 8 is a lateral view of a portion of the sleeve shown in FIG. 7.
Figure 9:
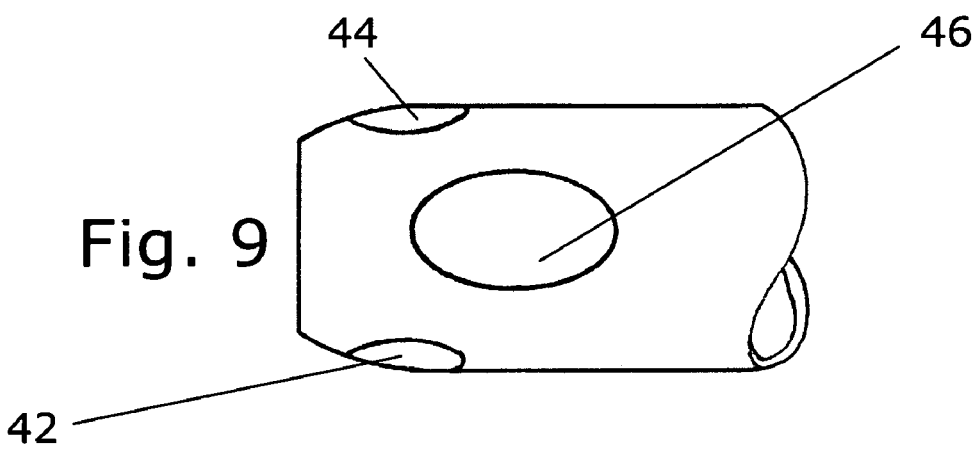
FIG. 9 is a bottom view of a portion of the sleeve shown in FIG. 7.

Referring to FIG. 7, a first embodiment of the present invention is shown wherein the tip of FIG. 4 has been modified to add a third infusion port 46. In this embodiment, infusion port 46 is oval in shape as can be seen in FIG. 9 and is positioned midway between infusion ports 42 and 44 as shown in FIGS. 7 and 9. FIG. 8 shows the position of infusion port 46 in a lateral view.

Referring now to FIGS. 10, 11 and 12, a second preferred embodiment is shown wherein infusion ports 48, 50, 52 are positioned equidistantly about the periphery of sleeve 54 and communicate with tip channel 56. FIG. 11 is a view taken in direction A as shown in FIG. 10, demonstrating the oval shape of infusion port 50. FIG. 12 is a view taken along direction B of FIG. 10 demonstrating the positioning and oval shape of infusion ports 48, 52.

As seen most clearly in FIG. 11, one portion of port 50 is formed through a straight portion 58 of sleeve 54 while a second portion is formed along the tapering section 60 of sleeve 54. A portion of port 50 is thus angled, at break line 62. This has the effect of directing a portion of the flow passing through port 50 away from the aspiration zone at the tip of the needle while allowing for a greater volume of infusion liquid to pass through at an even flow rate.

Figure 13:
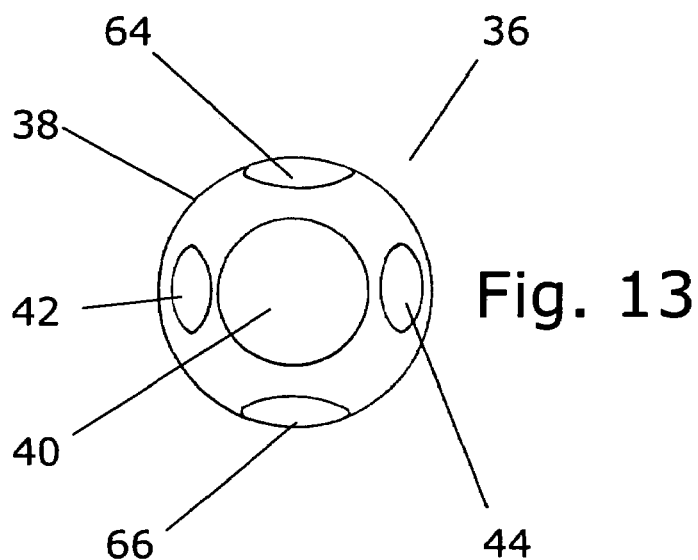
FIG. 13 is an end view of the sleeve of FIG. 4 modified to include four discharge ports.
Figure 14:
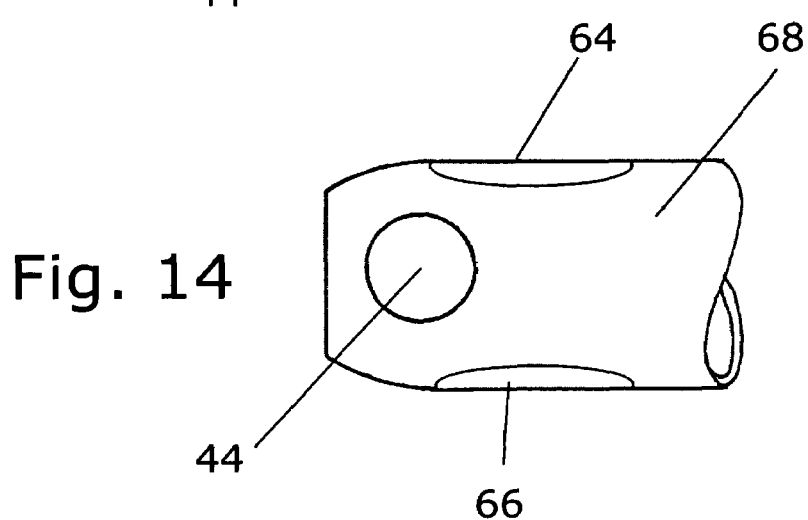
FIG. 14 is a lateral view of a section of the sleeve shown in FIG. 13.
Figure 15:
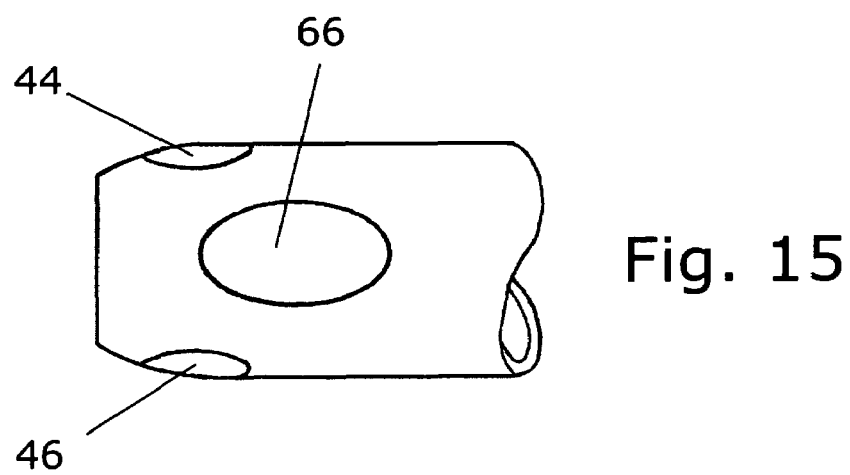
FIG. 15 is a top view of a portion of the sleeve shown in FIG. 13.

Referring now to FIGS. 13, 14 and 15, the fourth embodiment of the present invention is shown wherein an infusion sleeve of FIG. 4 is modified to add a pair of diametrically opposed infusion ports 64, 66. Infusion ports 64, 66 communicate with channel 40. As seen in FIG. 13, ports 42, 66, 44 and 64 are positioned equidistantly about the outer periphery of sleeve 36.

As seen in FIG. 14, infusion ports 64, 66 are positioned along the straight portion 68 of sleeve 36 and, as seen more clearly in FIG. 15, ports 64 and 66 are oval in shape.

Figure 16:
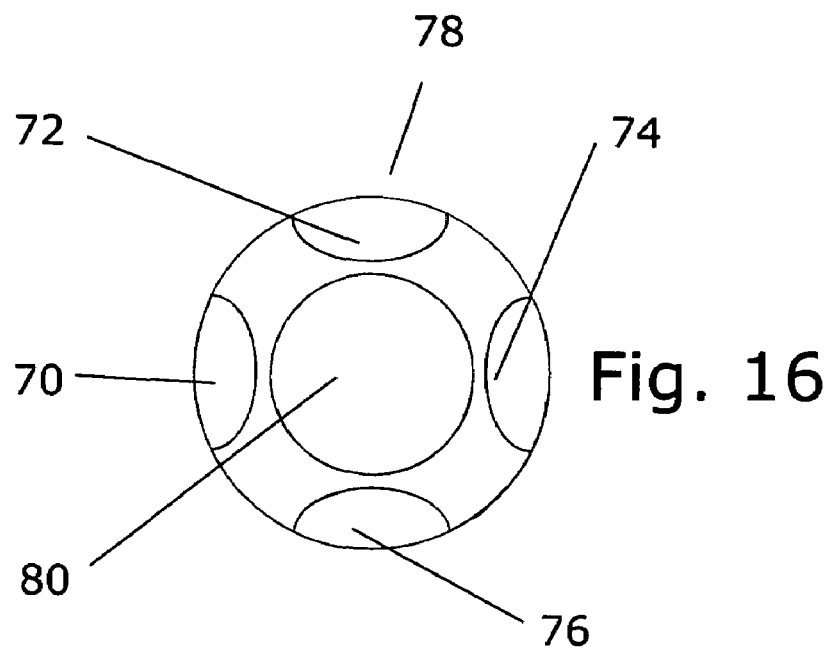
FIG. 16 is an end view of the embodiment of the present invention showing four oval discharge ports.
Figure 17:
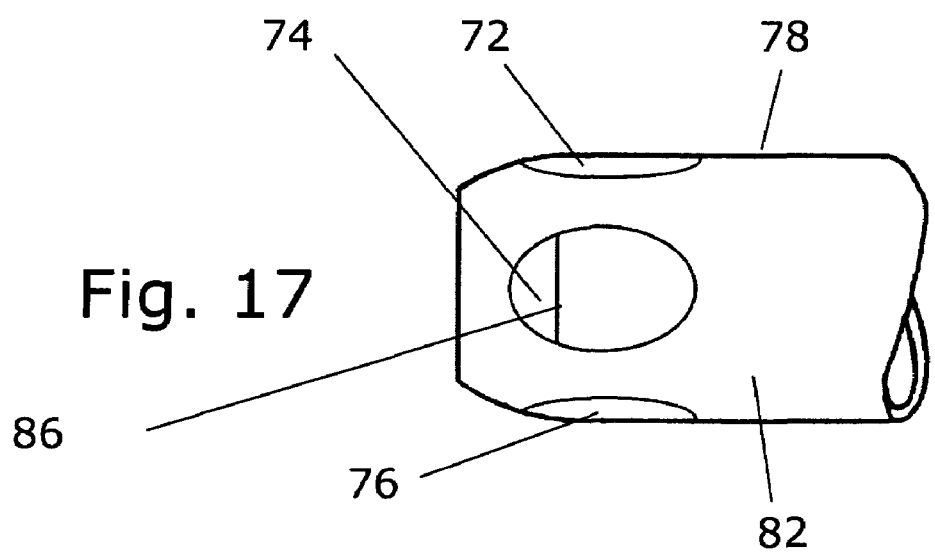
FIG. 17 is a lateral view of a portion of the sleeve shown in FIG. 16.
Figure 18:
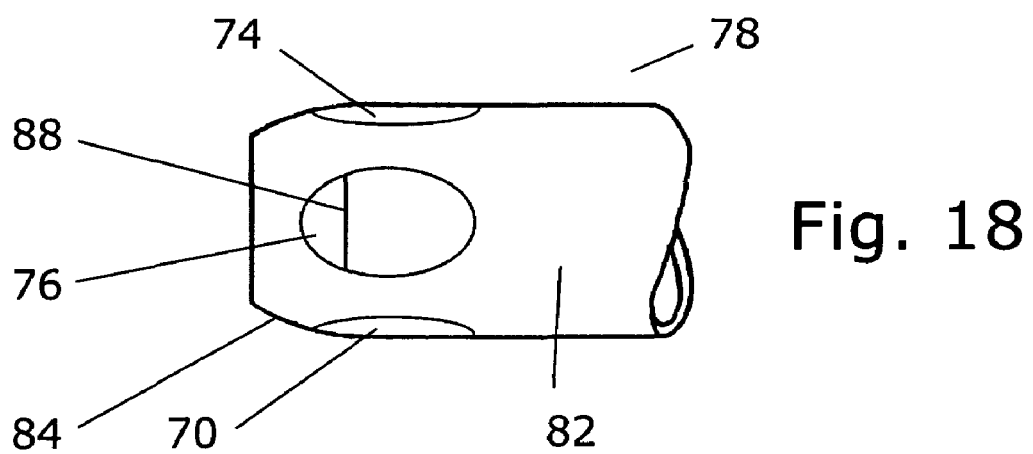
FIG. 18 is a top view of a portion of the sleeve shown in FIG. 16.

Referring now to FIGS. 16, 17 and 18, a fifth embodiment of the present invention is shown wherein a series of oval infusion ports 70, 72, 74 and 76 are positioned equidistantly about the periphery of sleeve 78. Each port 72, 74, 76 and 78 communicates with channel 80 of sleeve 78. As seen in FIG. 17, infusion port 74 is partially formed along a straight portion of straight portion 82 of sleeve 78 while the remaining portion is formed along a tapered portion 84 of sleeve 78, with port 74 angled at bend 86.

In like fashion, FIG. 18 shows that infusion port 76 is oval in shape and a portion of port 78 is formed on straight portion 82 of sleeve 78 while the remaining portion is formed through tapered portion 84 of sleeve 78, along bend 88.

Each of the infusion port arrangements shown in the foregoing figures has advantages over the prior art sleeves. One advantage is a measurable increase in the amount of infusion liquid that can be effectively injected through sleeve 36. For example, use of the original microsleeve with two circular diametrically opposed ports has been used at a flow rate of 100 ml per minute. By adding a third port it has been found possible to increase that flow rate to as much as 113 ml per minute.

It is contemplated that other variations in port size, number and positioning may also be used. As a general rule, the stiffer the material used to form the sleeve, the more ports may be used. Stiffer material will keep the sleeve from collapsing during surgery and touching the needle or otherwise affecting the rate of flow of infusing liquid through the sleeve.

What is claimed is:

1. In an infusion sleeve for use with a phacoemulsification handpiece, said handpiece having a phacoemulsification needle extending from a handpiece body, said infusion sleeve of the type having a hollow flexible tubular body with an open end through which said needle is inserted and an open tip through which said needle protrudes, said handpiece having a pathway through which irrigating liquid passes, said sleeve communicating with said liquid pathway to allow said liquid to pass through said sleeve when said sleeve is mounted to said handpiece, the improvement comprising:

at least three infusion ports through which said irrigating liquid is discharged,
said ports formed on said tubular body proximate said tip.

2. The apparatus as recited in claim 1 wherein said sleeve has three said infusion ports.

3. The apparatus as recited in claim 2 wherein said infusion ports are oval in shape.

4. The apparatus as recited in claim 2 wherein said infusion ports are spaced equidistantly from said tip and one from another.

5. The apparatus as recited in claim 2 wherein said two said infusion ports are equidistantly spaced from said tip and are spaced diametrically opposite one another.

6. The apparatus as recited in claim 5 wherein said two diametrically opposed infusion ports are round in shape and the remaining of said three ports is oval in shape.

7. The apparatus as recited in claim 1 wherein said sleeve has four said infusion ports.

8. The apparatus as recited in claim 7 wherein said four infusion ports are spaced equidistantly one from the other about the periphery of said sleeve.

9. The apparatus as recited in claim 7 wherein two of said infusion ports form a first pair and are spaced equidistantly one from another and equidistantly from said tip; and
the remaining two of said ports form a second pair and are spaced equidistantly one from another and from said tip.

10. The apparatus as recited in claim 9 wherein said first pair of ports is oval in shape.

11. The apparatus as recited in claim 10 wherein said four ports are spaced equidistantly from said tip and equidistantly one from another.

12. In an infusion sleeve for use with a phacoemulsification handpiece, said handpiece having a phacoemulsification needle extending from a handpiece body, said infusion sleeve of the type having a hollow flexible tubular body having an axis along which are formed an open end through which said needle is inserted and an open tip through which said needle protrudes, said handpiece having a pathway through which irrigating liquid passes, said sleeve communicating with said liquid pathway to allow said liquid to pass through said sleeve when said sleeve is mounted to said handpiece, the improvement comprising:

said sleeve being tapered toward said axis proximate said tip, said taper defined by a break formed on and extending around said sleeve proximate said tip;
at least three infusion ports through which said irrigating liquid is discharged,
said ports formed on said tubular body proximate said tip; and
at least one of said infusion ports formed across said break,
the remaining of said infusion ports formed such that said break is intermediate said remaining ports and said tip.

\* \* \* \* \*